United States Patent [19]

Hogan

[11] Patent Number: 5,135,792
[45] Date of Patent: Aug. 4, 1992

[54] DISPOSABLE, SELF-ENVELOPING AND SELF-CONTAINING ON-DEMAND, SUPERABSORBENT COMPOSITE

[75] Inventor: John D. Hogan, Gloucester, Mass.

[73] Assignee: Beth Israel Hospital Assoc., Inc., Boston, Mass.

[21] Appl. No.: 529,566

[22] Filed: May 25, 1990

Related U.S. Application Data

[63] Continuation-in-part of Ser. No. 445,008, Dec. 4, 1989, Pat. No. 5,061,285, which is a continuation-in-part of Ser. No. 142,077, Jan. 11, 1988, Pat. No. 4,885,000, which is a continuation-in-part of Ser. No. 1,648, Jan. 9, 1987, abandoned.

[51] Int. Cl.$^5$ .................................................. B32B 1/04
[52] U.S. Cl. .......................................... 428/74; 428/68; 428/76; 428/284; 428/913
[58] Field of Search ..................... 428/68, 74, 76, 284, 428/913

[56] References Cited

U.S. PATENT DOCUMENTS

| | | | |
|---|---|---|---|
| 4,675,217 | 6/1987 | Forsman | 428/74 |
| 4,921,743 | 5/1990 | Hansen et al. | 428/913 |
| 4,929,480 | 5/1990 | Midkiff et al. | 428/74 |
| 5,079,792 | 1/1992 | D'Haen | 428/74 |

Primary Examiner—James J. Bell
Attorney, Agent, or Firm—David Prashker

[57] ABSTRACT

A disposable, self-enveloping and self-containing on-demand superabsorbent composite is provided which is easily transportable, durable, and can be prepared in both sterile and non-sterile formats. The disposable composite provides a fluid absorbing capacity via fibers able to absorb not less than 15 times their own weight in fluid and preferably are able to absorb at least 50 times their own weight in fluid and other liquid wastes. The composite can be prepared in various formats and styles for use in both hospitals, ambulances, emergency medical personnel, and by morticians and funeral directors as well.

11 Claims, 8 Drawing Sheets

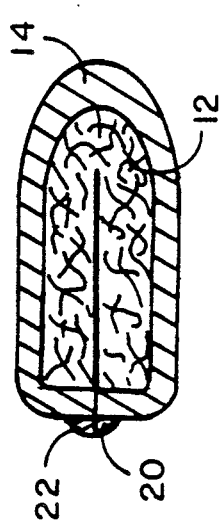
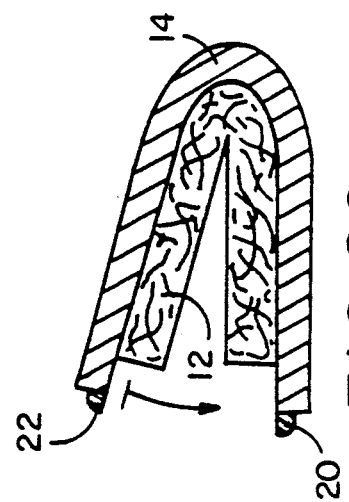
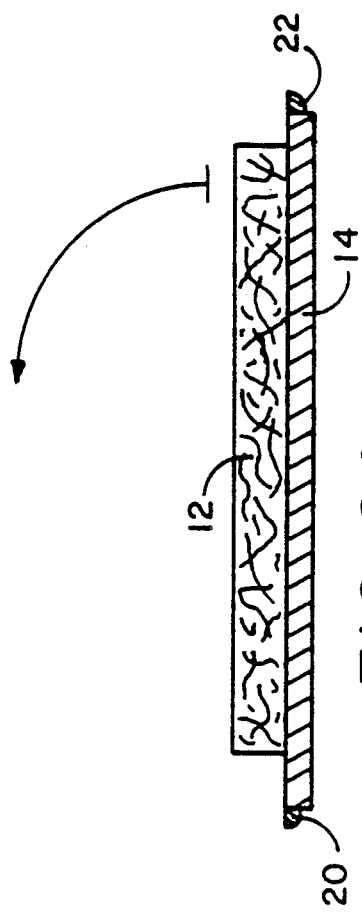
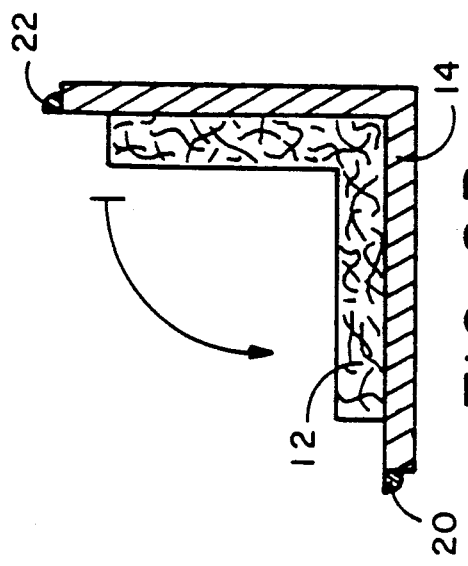

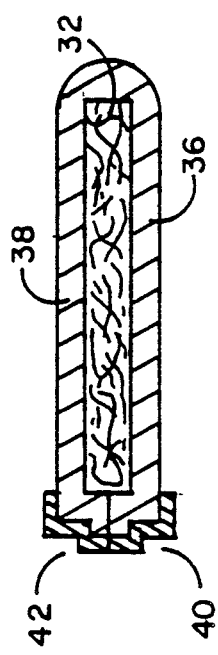
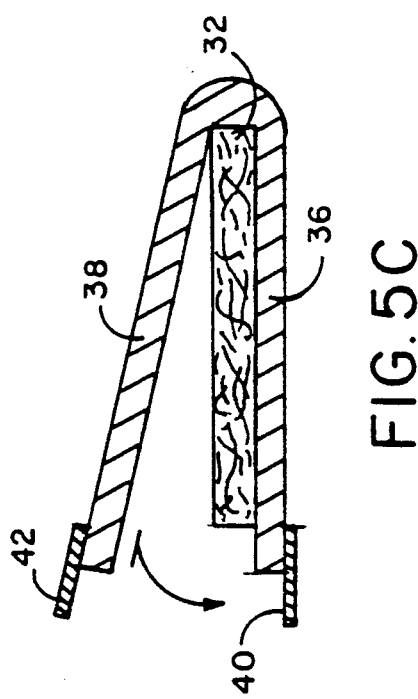
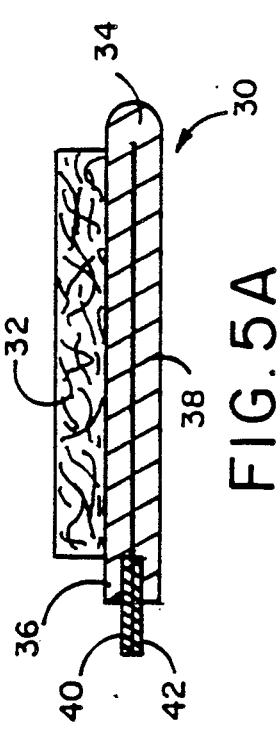
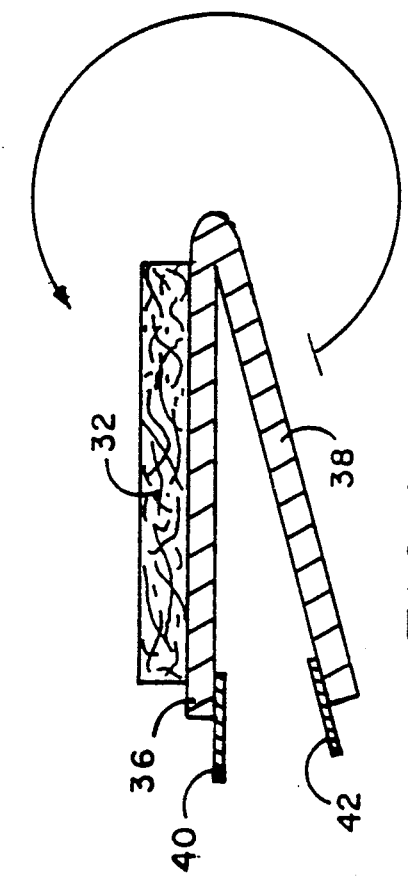

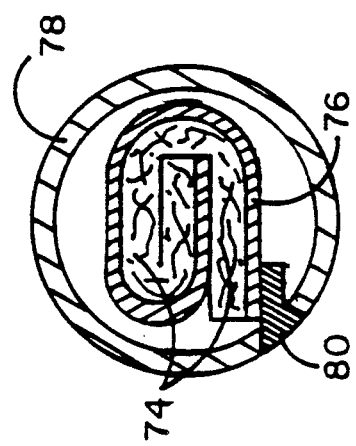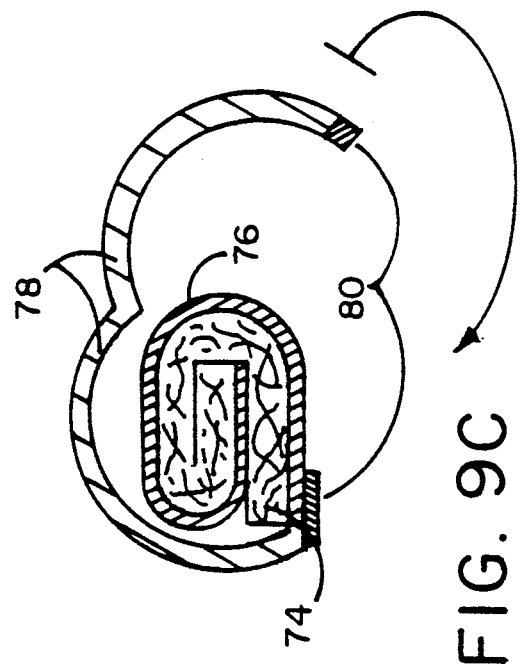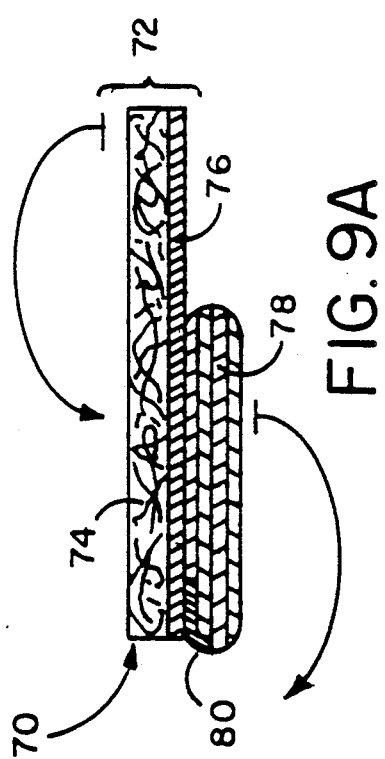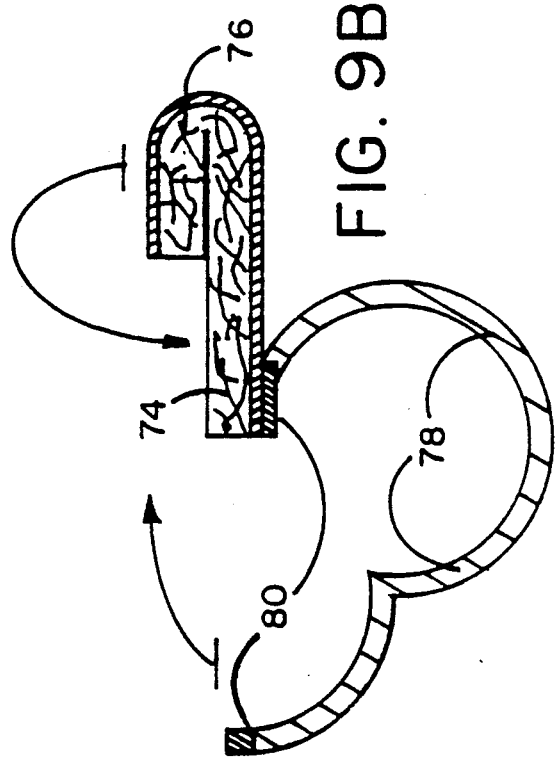

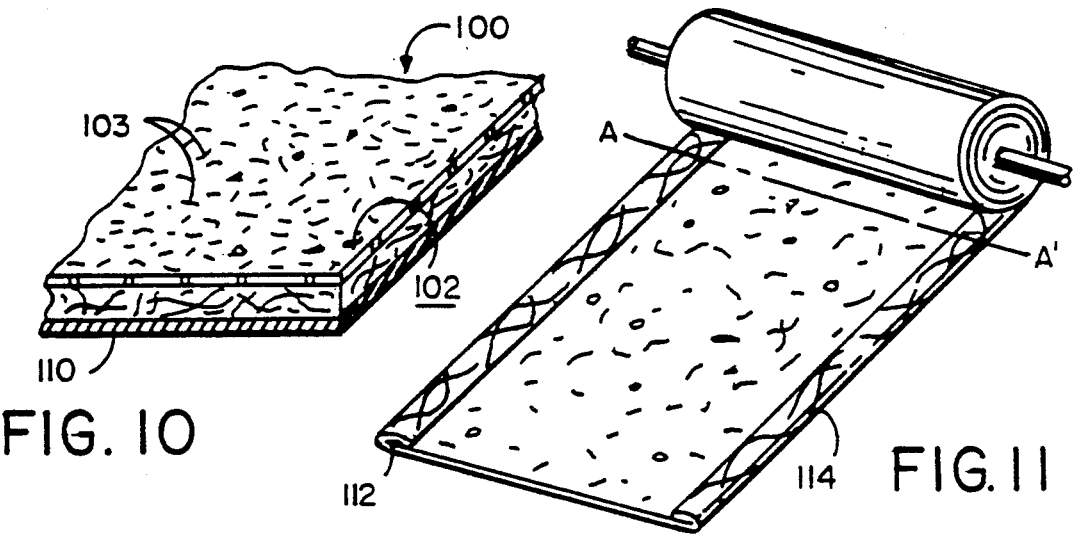
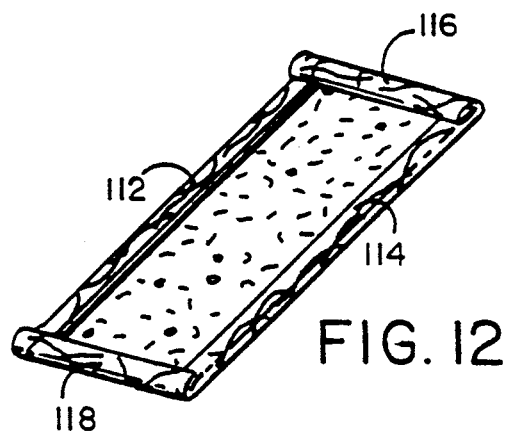
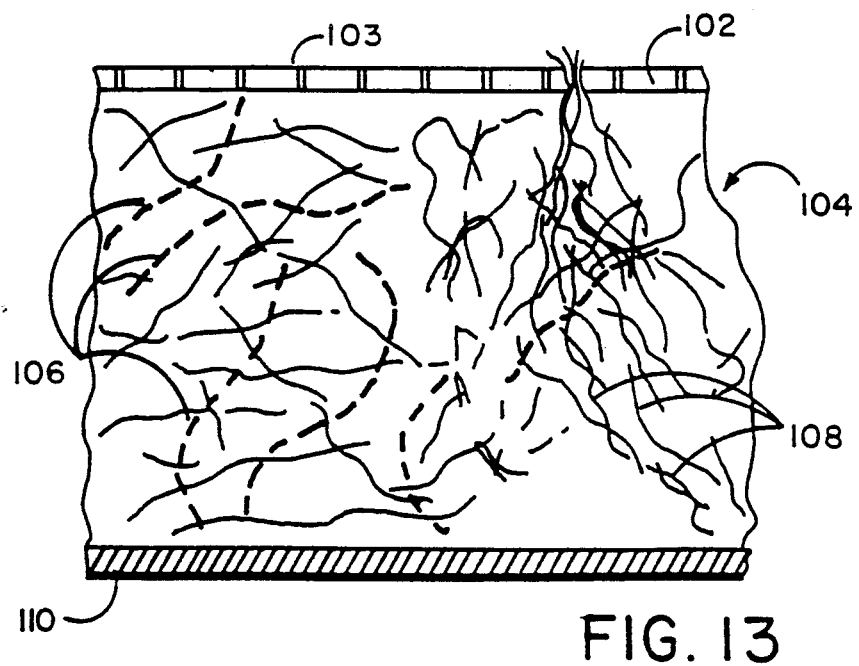

DISPOSABLE, SELF-ENVELOPING AND SELF-CONTAINING ON-DEMAND, SUPERABSORBENT COMPOSITE

CROSS-REFERENCE

The present application is a continuation-in-part of application Ser. No. 445,008 filed Dec. 4, 1989, now U.S. Pat. No. 5,061,285, which is a continuation-in-part of application Ser. No. 142,077 filed Jan. 11, 1988, now U.S. Pat. No. 4,885,000 issued Dec. 5, 1989, which was a continuation-in-part of application Ser. No. 001,648 filed Jan. 9, 1987, abandoned.

RESEARCH SUPPORT

The research for the present invention was supported by the Beth Israel Hospital Association.

FIELD OF THE INVENTION

The present invention is concerned generally with improvements in fabrics, textiles, and cloths commonly used by emergency medical personnel and technicians in ambulances, emergency rooms, and trauma centers; and is particularly directed to improvements in absorbent sheeting and bedding which markedly reduce the risk of accidental infection and contamination of personnel from potentially hazardous body fluids and liquid waste released by an infected or injured subject both during life and after death.

BACKGROUND OF THE INVENTION

It is commonly recognized that persons who have been traumatically injured or are afflicted by disease or a disorder have physical injuries and/or gross symptoms which are typically accompanied by the release of potentially infectious blood and other body fluids which may harbor bacteria, viruses, or other hazardous and toxic agents. The variety of potentially hazardous body fluids and liquid wastes includes not only infectious blood, lymph fluid, sputum, and the other body fluids comprising or protecting the major tissues and organs internally; but also urine, excrement, fouled water, ambient hazardous chemicals and toxic agents, mud and other soil mixtures, as well as other major parts of the environment in which the individual works or lives. These potentially hazardous fluids and wastes may then contaminate, injure, or infect any and all persons coming into contact with these fluids including the emergency medical personnel; orderlies, nurse's aides, and service personnel; other patients and persons in the general environment; and the pathologists and attendants examining the body tissue or performing the autopsy. This is especially the case when a lethal and possibly contagious agent or disease was the true cause of death.

It has now been well recognized that current procedures for removing potentially hazardous body fluids and liquid wastes released by a living or dead person during medical treatment or via autopsy are often inadequate, inefficient, or actually hazardous. Often, body fluid and liquid waste is absorbed only via the use of bulky sheets or drapes with minimal absorptive capacity; such articles can not usually absorb the quantity of fluid released and typically allow the unabsorbed fluid and other liquid waste to drip freely onto the surrounding environment and supporting personnel. This is particularly the case when the subject is moved from place to place.

A repetitious and continuing problem with current procedures and practices is the unintended, accidental contact with potentially hazardous fluids and wastes by the unknowing and/or uninformed person. Even when "universal precautions" procedures dictate the use of a central receptacle for the deposit of potentially dangerous materials and items, the difficulty remains in that each person using the central receptable comes into inadvertent and unknowing contact with the hazardous fluids and wastes previously deposited by others. Every time the central receptable is opened, each person in turn can become accidently exposed to the air particulates released by the previously deposited fluids and wastes already present. Such exposure occurs regularly because none of these deposited materials have been individually isolated or contained in advance of their being deposited into the central receptacle. In common practice, the potentially hazardous fluids and wastes often intermix and commingle within the confines of the central receptacle, thereby often actually increasing the risk of accidental contamination for the next person to open the receptacle to make a deposit.

In many instances, also, when unfortunately the subject has died of his injuries or disease, it is then desirable to protect the living from the fluids released by the corpse of the subject. Nevertheless, particularly in autopsy and embalming procedures, the potentially hazardous body fluids and liquid waste is in direct contact with personnel and is often allowed to drain directly into septic systems. These conventionally known procedures frequently lead to contamination of the skin, clothing, and person of the attending personnel; and all too often to contamination of the equipment, furniture, and the general surrounding environment where the corpse is held. In such instances, it is extremely important to employ effective precautions to protect the physicians during autopsy and the embalming personnel, especially when a lethal and possibly contagious disease was the cause of death of the subject.

The severity of this problem is best illustrated and understood by following the normal course of events which typically occur after a call for an ambulance or emergency medical personnel has been initiated to a particular site. A standard part of the equipment that ambulance and emergency medical personnel bring to the wounded or infected person is a stretcher - destined for aiding and supporting the injured or sick person from the original site where found to an emergency room or trauma center. The conventional stretcher is an upholstered or cushioned bed supported on a frame and has wheeled collapsible legs which aid in the moving of the body of the person after placement on the stretcher. All too often the stretcher itself is covered merely with a thin fibrous sheets and/or blankets upon which the injured or infected person is placed.

After the patient is placed on the stretcher, the medical attendants typically roll up the side of the sheet and blanket to prevent the body fluids (including blood and human waste) from dripping or actually flowing onto their person or from splattering the general environment surrounding the place where the patient has been found. Note that the blood and other fluid typically dripping from the bedding is due in part to the weight of the patient. When the patient is physically picked up for transfer, the weight of the person causes the sheets to form a hammock thereby forming a valley into which fluids run. Also, the weight of the patient actually squeezes fluid out of the wetted bedding during handling and transfer.

As an aid, absorbent padding is in common use by emergency personnel and typically appears in the form of wedges, bolts, sponges, or other shapes of cloth placed along the perimeter or edges of the stretcher to help prevent the dripping of the potentially hazardous fluids and to minimize the contamination of the local geographical area. Many of these aids incorporate fluid-absorbing materials, often in powdered or particulate form. Unfortunately, such conventionally used aids have major deficiencies. Frequently they absorb only limited amounts of fluids, typically only a maximum of 10 fold its weight in water or other fluids. Moreover, many of these absorbent aids are not readily fixed in place within a fibrous weave or cloth; consequently, when wet, these materials tend to clump and displace in volume and position. Equally important, even the recently introduced "gel blocks" become far less absorbent when the top of the material becomes saturated thus causing the product to ooze and dispel fluid when saturated, particularly under pressure circumstances. In addition, these gel block products typically wick fluid across their top surfaces, and thus may actually increase the risk of potential contamination of the entire fluid absorbing material and the medical personnel holding them in position. Thus, the present emergency and ambulatory practices do not provide effective, portable materials or apparatus by which to protect attending personnel from the fluids released by the injured (or perhaps even dying person) while lying on the stretcher during initial examination at the site of injury or discovery, or during transport to the hospital emergency room or trauma center.

Another critical event typically occurring upon entering the receiving room of the hospital or trauma center is a physical transfer by medical personnel of the patient from the portable stretcher bed to a fixed examination table. Once the injured or diseased person has been placed upon a hospital examination table, he then may be isolated as required or necessary using known isolation tents or other isolation apparatus. The bedding, however, upon which the patient lies then accompanies him during the subsequent transfers to other tables, gurneys, and other stretchers or litters to isolation wards, surgical operating rooms, post-surgery re-covery rooms, etc.; this bedding remains a serious risk to medical personnel because of the continuing release of potentially infective blood and other body fluids during the emergency treatment process.

In addition, following an emergency treatment procedure where a certain amount of urgency and disciplined chaos are frequently present, a variety of sharp-edged articles such as scalpels, syringe needles, and the like may accidently become lost or intermingled in the bedding. After the patient has been physically moved onto a different stretcher (as in the emergency room), someone else comes to clean up the debris left in the aftermath. This person, while in the act of gathering up the sheets and bedding, frequently is punctured by a hidden sharp-edged instrument inadvertently left in the sheets or bedding; and thus can become accidentally infected by the infectious blood, fluids, and other wastes on the instrument and in the surrounding bedding.

The sequence of events taken to its undesirable but logical conclusion ends in the autopsy room for the pathological workup and report. Unfortunately, there is a major risk of infection for autopsy personnel which can occur both during the performance of the autopsy and during the subsequent cleaning-up process. Blood spills, pieces of tissue, and other fluid and liquid matter associated or obtained via the autopsy can soil personnel clothing, surrounding equipment, tables, and even the floors within the autopsy room—hereby creating major risks of contamination and infection to involved personnel.

It is abundantly clear, therefore, that the risk of potential contamination, infection, and other direct injury remains a real and relatively constant threat and danger to medical personnel and other persons coming into contact with the hazardous fluids and wastes from either the living injured or diseased person, or the subsequent corpse. It is now also recognized that the broad variety of known innovations, customary protective measures, and conventional tangible means for protecting personnel are in the main limited to specific use circumstances of relatively short duration and effectiveness; and moreover, are not themselves useful or convenient for prolonged use or effect.

A summary review of the presently available protective devices and absorbent articles reveals the inherent limitations and general unsuitability of these conventionally known devices and articles to protect the individual person from the fluids and wastes released by persons afflicted with injury or disease. For example, a variety of fluid-absorbent fabrics and fibers are known which are conventionally used both as wound dressings and as protective garments in the operating room. These are described by: British Patent No. 2,175,210; French Patent No. 2,565,110; and U.S. Pat. Nos. 4,748,065; 4,637,820; and 3,521,624.

Despite these fabrics and fibers, there remains a demonstrable and long standing need for an absorbent textile article or gauze-like commodity which has the capability of being self-enveloping, self-containing, and safely disposable on demand; and prevents the dripping and flow of fluids such that the attending medical personnel and the surrounding environment remain substantially free from and protected from the effects of potentially hazardous body fluids and liquid wastes released by the injured, diseased, or deceased person being attended. Insofar as is presently known, there is no single article or commodity which is able to be utilized not only at the first instance of finding, discovering, or treating an injured or diseased person; but also is able to be emplloyed in a variety of formats through the subsequent events up to and including autopsy and funeral disposition.

SUMMARY OF THE INVENTION

The present invention is a disposable, superabsorbent composite which is self-enveloping, self-containing, and self-closing on demand. This composite comprises: at least one disposable, superabsorbent fibrous layer containing fluid-absorbing fibers able to absorb not less than fifteen times their own weight of fluid; disposable, on-demand enveloping and containing means joined to at least a portion of the superabsorbent fibrous layer, these means being able to envelope and contain the superabsorbent fibrous layer on-demand; and on-demand closure means joined to the enveloping and containing means for closure of the enveloped and contained superabsorbent fibrous layer.

The superabsorbent composite can be shaped into a number of different formats and articles which can include: superabsorbent sheets, blankets and bedding; superabsorbent pads, sponges, wedges, bolts, and cloths; and superabsorbent flooring, drapes, partitions, and envlosures. Each of these commodities is self-enveloping, self-containing, and self-closing on-demand; and each can be pre-sterilized before use and-/or post-sterilized after use in accordance with the needs or desires of the user.

BRIEF DESCRIPTION OF THE FIGURES

The present invention may be more easily and completely understood when taken in conjunction with the accompanying drawing, in which:

FIGS. 2A-2D are cross-sectional views of the embodiment of FIG. 1 illustrating the sequence of events for converting the superabsorbent composite from the open state into the self-enveloped and self-contained state;

FIGS. 5A-5D are cross-sectional views of the second embodiment of FIGS. 3 and 4 illustrating the sequence of events for converting the superabsorbent composite from the open state into the self-enveloped and self-contained state;

FIGS. 9A-9D are cross-sectional views of a fourth preferred embodiment of the superabsorbent composite illustrating the sequence of events for converting the embodiment from the open state into the self-enveloped and self-contained state;

FIG. 10 is a perspective view illustrating a preferred three component laminated sheet construction comprising the superabsorbent fibrous layer of FIGS. 6-9 respectively;

FIG. 11 is a perspective view of a prepared roll of the three component laminated sheet of FIG. 10;

FIG. 12 is an illustration of the preferred manner of using the three component laminated sheet of FIG. 10; and FIG. 13 is a detailed cross-sectional view of the three component laminated sheet of FIG. 10.

DETAILED DESCRIPTION OF THE PREFERRED EMBODIMENTS

Figure 1:
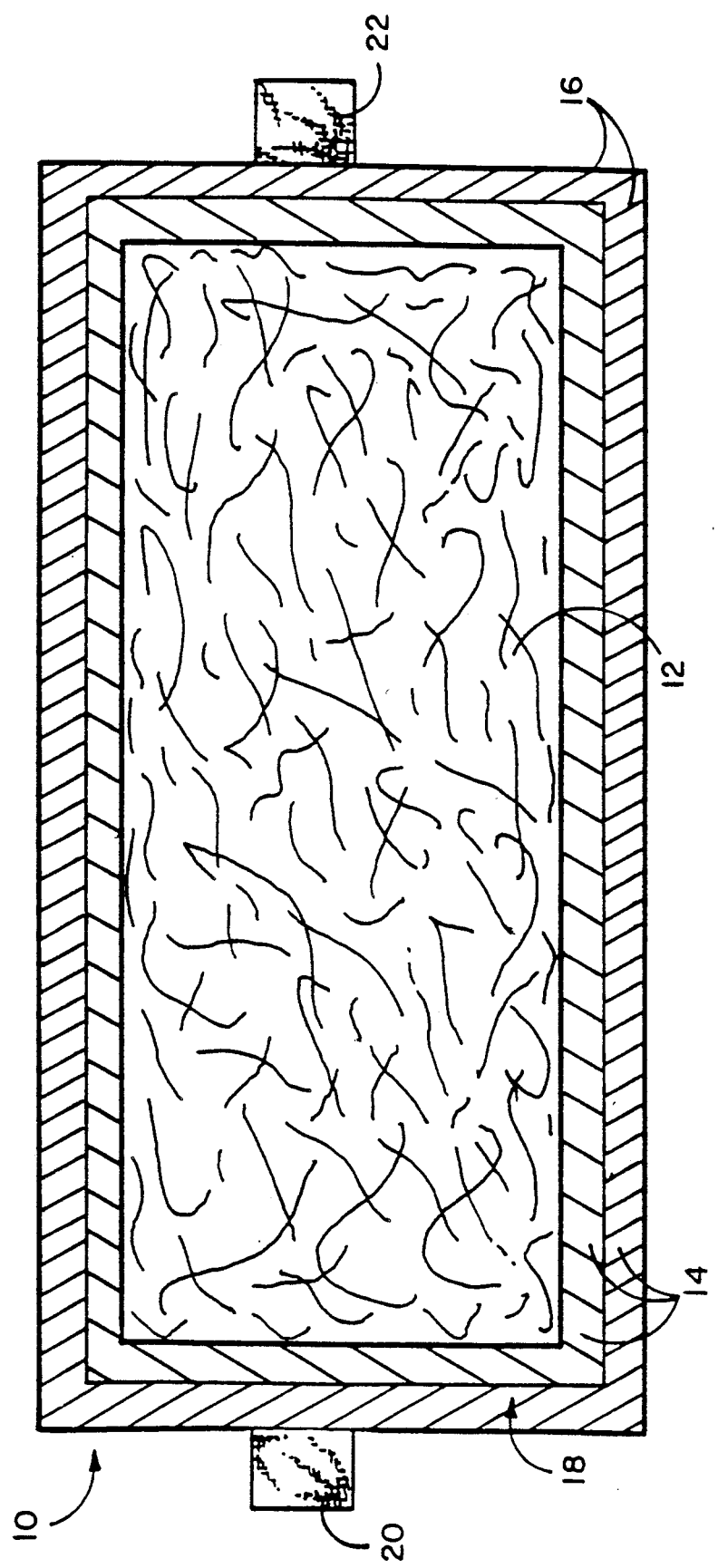
FIG. 1 is an elevated overhead view of one preferred embodiment comprising the superabsorbent composite of the present invention.

The present invention is a superabsorbent commposite prepared as a single, unitary article to be self-enveloping and self-containing on-demand. The article can be constructed in a variety of different ways to meet and to accommodate diverse uses and applications.

Accordingly, the broadest definition of the superabsorbent composite comprises at least one disposable, superabsorbent fibrous layer containing fluid-absorbing fibers able to absorb not less than fifteen times their own weight of fluid; on-demand enveloping and containing means joined to at least a portion of the superabsorbent fibrous layer, these means being able to envelope and contain the superabsorbent fibrous layer on demand; and on-demand closure means joined to the enveloping and containing means for closure of the enveloped and contained superabsorbent fibrous layer.

In addition, an alternative definition of the superabsorbent composite comprises: a disposable, superabsorbent, laminated sheet comprised of: (a) at least one superabsorbent fibrous layer containing fluid-absorbing fibers able to absorb not less than fifteen times their own weight of fluid; and (b) a fluid-impermeable material applied to one surface of the fibrous layer; disposable, on-demand enveloping and containing means joined to at least a portion of said superabsorbent laminated sheet, these means being able to envelope and contain the superabsorbent laminated sheet on-demand; and on-demand closure means joined to the enveloping and containing means for closure of the enveloped and contained superabsorbent laminated sheet.

It is expected that the configurations, dimensions, volumes, surface areas, manner of envelopment and containment, means for closure and/or sealing after containment, and mode of disposal will be different and variable for each embodiment. Clearly, when prepared as superabsorbent sheets, blankets, and bedding, the superabsorbent composite will be larger in dimensions and surface area, often be thicker, be more dense, and typically weigh more than other constructions. Alternatively, when prepared as superabsorbent pads, sponges, wedges, bolts, or cloths, the superabsorbent composite will typically be dimensioned to be hand-held, be lightweight, and often be made in both thicker and thinner formats for larger and smaller volume absorbency. Finally, when prepared as superabsorbent flooring, drapes, or temporary partitions and enclosures, the composite will likely be dimensioned as large, moderate-weight squares, rectangles, ovals, or other shaped articles of medium thickness and varying density.

Each embodiment of the present invention is intended to be constructed in advance; can be carried and transported as a discrete article in a prepackaged rolled or folded form or as an unpackaged open/bulk form; and be prepared in either a pre-sterilized or non-sterilized state. Upon reaching the intended site of use, person, and/or application, the composite will serve effectively in the desired setting; and act as a superabsorbent article to protect the patient, attending personnel, and general public. Subsequent to its intended use, the superabsorbent composite is constructed to be self-enveloping, self-containing, and self-closing (and optionally self-sealing) on-demand upon the wish or need of the user. Once self-enveloped and self-contained, the composite is easily disposable, with or without post-use sterilization, in accordance with routine disposal procedures.

By the variety of constructions and the diversity of intended applications for the superabsorbent composite, it will be recognized and appreciated that the present invention provides multiple, major, and unique benefits and advantages which were not previously known or available by conventionally used articles. These include:

1. The present superabsorbent composite is easily portable, durable, self-enveloping, and self-containing on demand; and is disposable in a manner consistent with presently employed routine procedures. The article can be configured, dimensioned, and constructed to serve many different functions and uses under a wide variety of different locations, settings, and circumstances including: emergency ambulatory personnel; hospital physicians and surgeons and nurses; pathologists and autopsy-room technicians; as well as morticians and funeral directors.

Among the diverse functions and applications for the superabsorbent composite are the following: A temporary isolation bed or intensive care unit bed in remote areas or in instances of natural disasters, epidemics, or tragic accidents; a military medical bed in the field, or as a temporary partition or enclosure aboard ship which would keep patients protected from the environment as well as from infecting each other; a temporary shelter to protect the injured such as an injured skier from climatic conditions including snowstorms and cold; and as a regularly used hospital bed for persons such as AIDS patients to avoid contamination of mattresses and other permanent hospital equipment and fixtures. Many other use circumstances are envisioned in addition to these.

2. The present invention is a superabsorbent gauze-like commodity comprising a fibrous layer able to absorb at least 15 times and preferably up to 50 times its own weight of fluid. In some preferred embodiments, the superabsorbent fibrous layer is formed as a multi-laminate sheet construction which optionally can be detached and replaced at will by another similarly sized laminated sheet cut from a prepared roll or bolt as needed. In this manner, the superabsorbent fibrous layer of the composite employed on one occasion may—at one's option and choice—be easily substituted and replaced by another similarly configured and dimensioned one without discarding or disposing of the other parts of the composite comprising the present invention as a whole.

3. The superabsorbent composite can be disposed at will at any time after a single use or after multiple use occasions. The article—then containing and holding fluids and other liquid waste released by the body or otherwise absorbed by accidental or inadvertent fluid contact within the superabsorbent fibrous layer—will not drip, flow, or otherwise release fluid over the volume or perimeter of the article itself. The used composite, now containing substantial quantities of fluid and other liquid waste, may nevertheless be folded or rolled into a self-enveloped and self-contained format; and then be discarded or destroyed completely as a single unitary article without any danger of accidental contamination or spillage from the absorbed contents.

Preferred Embodiments

Some preferred embodiments of the present invention are illustrated via FIGS. 1-9 inclusive. As illustrated therein, FIG. 1 provides an overhead elevated view of one preferred embodiment of the superabsorbent composite in its simplest format. FIGS. 2A-2D illustrate the features and component parts of the commodity; and demonstrate the ability of the article to become self-enveloping and self-containing on demand.

As seen in FIG. 1, the present invention appears in the format and construction representative of a superabsorbent pad, sponge, wedge, bolt, or cloth. The actual dimensions of this embodiment are typically proportioned such that the composite preferably can be handheld or hand-controlled; be relatively light weight; and be prepared in both thicker and thinner formats for absorbance of either larger or smaller fluid volumes. The composite 10 is comprised of a superabsorbent fibrous layer 12 which is disposed upon a supporting cover or stratum 14. The superabsorbent fibrous layer 12 is comprised of fluid-absorbing fibers able to absorb not less than 15 times their own weight of fluid. The fibrous layer 12 illustrated within FIG. 1 is the bare superabsorbent layer alone; alternatively, the bare fibrous layer may be substituted by a disposable superabsorbent laminated sheet construction comprised of at least one superabsorbent fibrous layer and a fluid-impermeable material applied to one surface of the fibrous layer. The supporting cover 14 is desirably composed of a fluid impermeable natural or synthetic material which is flexible and durable; and provides the requisite tensile strength to function as a support for the superabsorbent fibrous layer 12. It is preferable that the dimensions of the supporting cover 14 be larger than the dimensions of the superabsorbent fibrous layer 12 in order that a narrow perimeter space 16 surround the edges of the fibrous layer 12.

In this simplest embodiment, an adhesive substance 18 has been applied to at least a portion of the narrow perimeter space 16 comprising one surface of the supporting cover 14. In addition, a pair of sealing tabs 20,22 are optionally attached to the edge of the supporting cover 14. The exposed outer surfaces of the sealing tabs 20,22 have also been preferably coated with the adhesive substance 18. It is also desirable that narrow strips of paper, plastic, or other non-binding matter (not shown) be applied over the adhesive substance 18; and in this manner, the strips will cover and protect the adhesive substance 18 from accidental contact until an appropriate time.

It will be recognized that within the embodiment of FIGS. 1 and 2, the on-demand enveloping and containing means are provided by the narrow perimeter space 16; by the exterior of the supporting cover 14; by the adhesive substance 18 applied to the surface of the perimeter space 16; and optionally by the sealing tabs 20 and 22. It will be appreciated also that the use of an adhesive substance is merely one conventional means for allowing the edges of the supporting cover 14 to be joined together on-demand; and that many other generally known and commonly employed means for joining the edges of the supporting cover together, with or without use of the perimeter space 16 or the sealing tabs 20 and 22, may be substituted and used in place of an adhesive substance. Representative of such generally known and commonly employed joining means are: ties, snaps, hooks, velcro cloth strips, buttons, "zip-lock" closures, and the like.

The present invention ready for use as a fluid absorbing article is shown in FIGS. 1 and 2A. When employed as a pad, sponge, cloth, and the like, the superabsorbent fibrous layer 12 of the composite 10 will absorb great quantities of liquid in volumes not less than 15 times their own weight and often up to 50 times their own weight of fluid. The composite 10 may be employed fibrous layer side up or down as the circumstances require; and may be twisted, folded, or rolled if needed. Regardless of the contortions or twistings, the superabsorbent fibrous layer will continue to absorb fluid, liquid, and/or wastes including blood, lymph, fluid, sputum, and other body fluids as well as urine, excrement, foul water, mud and other soil mixtures, and any other potentially hazardous fluids which may be present.

After the gauze commodity has been used to absorb body fluids and/or other liquid wastes, the article becomes self-enveloped, self-contained, and self-closed on demand. As shown by the sequence of events illustrated by FIGS. 2A-2D, the supporting cover or stratum 14 serves as the enveloping and containing means for the composite. Initially, the protective strips covering the adhesive substance 18 applied to the narrow perimeter space 16 are removed. The commodity is then desirably folded as shown by FIGS. 2B and 2C respectively. By continuing the folding of the supporting cover 14 upon itself, the applied adhesive substance 18 along the perimeter space 16 of the supporting cover 14 comes into contact with itself. In this manner, the edges of the supporting cover 14 become attached to each other along the perimeter space 16 thereby enveloping and containing the soiled fibrous layer 12 completely and securely. By continuing the folding procedure to completion as illustrated by FIG. 2D, the sealing tabs 20,22 optionally present have been folded over one another thereby effecting not only a complete closure of the supporting cover 14, but also providing an effective fluid-tight seal for the composite as a whole. As seen within FIG. 2D, the soiled superabsorbent fibrous layer 12 is completely enveloped, contained, and effectively sealed within the supporting cover 14. The fluid contents within the enveloped and contained fibrous layer 12 can not escape from containment and are effectively sealed within the enveloping, containing supporting cover 14 in a manner which allows for safe disposal in accordance with routine procedures.

Figure 3:
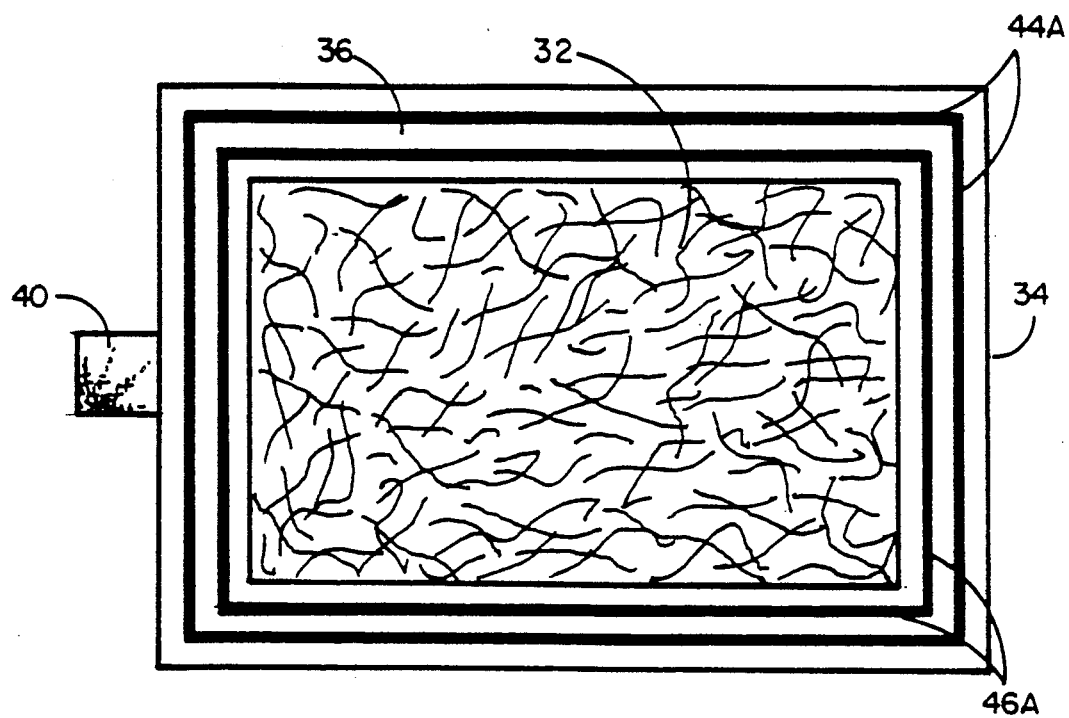
FIG. 3 is an overhead elevated view of a second preferred embodiment of the superabsorbent composite.
Figure 4:
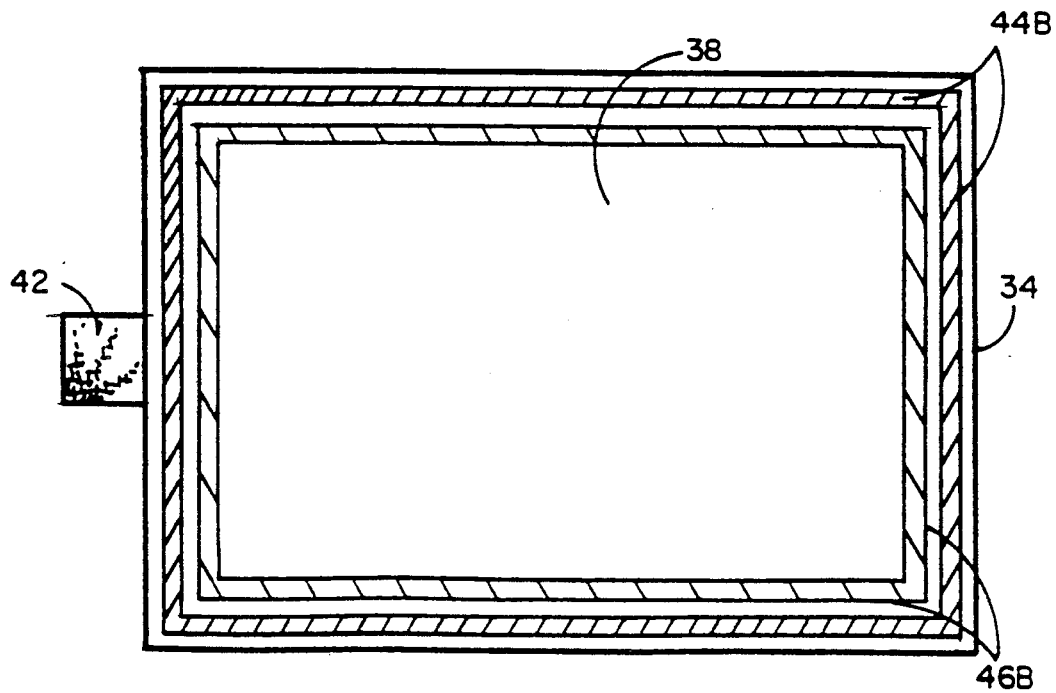
FIG. 4 is a bottom elevated view of the superabsorbent composite of FIG. 3.

A second preferred embodiment of the superabsorbent composite comprising the present invention is illustrated by FIGS. 3-5. Top and bottom elevated views are shown in FIGS. 3 and 4. Cross-sectional views of the second embodiment constructed for intended use as superabsorbent flooring, drapes, or temporary partitions and enclosures and the sequence of events performed immediately prior to disposal are shown by FIGS. 5A-5D. In this embodiment and format, the superabsorbent composite 30 is comprised of a superabsorbent fibrous layer 32 disposed upon a supporting cover or stratum 34 which has been purposefully folded upon itself in advance to form a double stratum of two half covers 36,38 respectively. Optionally attached to one edge along the perimeter of each half cover 36,38 are sealing tabs 40,42 which are initially positioned together until the user wishes to separate them. As noted previously, the superabsorbent fibrous layer 32 is again dimensioned in length and width to be somewhat smaller than the dimensions of the supporting cover 34 in its entirety. In this embodiment, however, the perimeter of the supporting cover 34 is preferably formed with a series of aligned raised ribs 44a,46a on the half cover 36 which are in positional correspondence and alignment with the enveloping cavities 44b,46b on the half cover 38. The aligned ribs 44a,46a and the cavities 44b,46b are unobtrusive and do not interfere with the intended function of the superabsorbent composite as flooring, drapes, and the like. Alternatively, any other means for juncture may be applied to the perimeter edge of the supporting cover 34 in a manner similar to that illustrated within FIGS. 3 and 4 herein.

The composite appearing in FIGS. 3, 4, and 5A is ready for immediate use. It can be dimensioned as a rectangular, square, or oval flooring mat; as a specifically configured drapery; or as a temporary partition or enclosure to be supported by a previously constructed frame or wall as the circumstances require or permit. The superabsorbent fibrous layer 32 of the composite will absorb not less than 15 times its own weight in fluids; and will thus serve to absorb any and all possible splatterings, drippings, drainage—thereby protecting both the patient and the attending personnel from accidental contact and contamination with potentially hazardous fluids. The time and longevity of service for the composite is expected to vary markedly; the duration of function and value will clearly depend upon the exigencies of the use circumstances.

When the user determines or desires that the superabsorbent composite is no longer of value or service, the fibrous layer 32 may be enveloped and contained on-demand via the sequence of events illustrated by FIGS. 5B, 5C, and 5D respectively. As seen therein, the optionally present sealing tabs 40,42 are separated; and the two half covers 36,38 are purposefully distanced from one another. One half cover 38 is purposefully rotated as illustrated by FIGS. 5B and 5C such that the supporting cover 34 completely envelopes and contains the soiled superabsorbent fibrous layer 32. As noted previously, the supporting cover 34 is composed of a flexible, fluid impermeable material and thus serves as a enveloping and containing stratum to hold the soiled fibrous layer 32 completely and securely. The perimeter edges of the supporting cover 34 comprising raised ribs 44a,46a and enveloping cavities 44b,46b in aligned positions or other closure means conventionally known in this art are joined together thereby forming the supporting cover 34 into an envelopment and containment stratum which completely encloses the now soiled fibrous layer 32. Furthermore, as illustrated by FIG. 5D, the sealing tabs 40,42 thus provide an effective fluid-tight seal for the article as a whole. The entirety of the used superabsorbent composite may now be disposed in any manner consistent with good practice.

Figure 6:
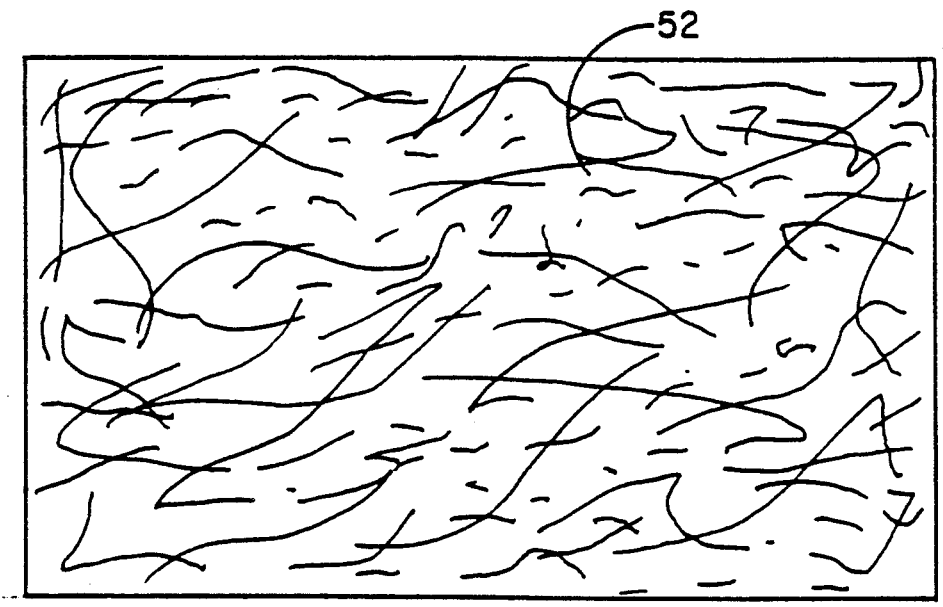
FIG. 6 is an overhead elevated view of a third preferred embodiment of the superabsorbent composite.
Figure 7:
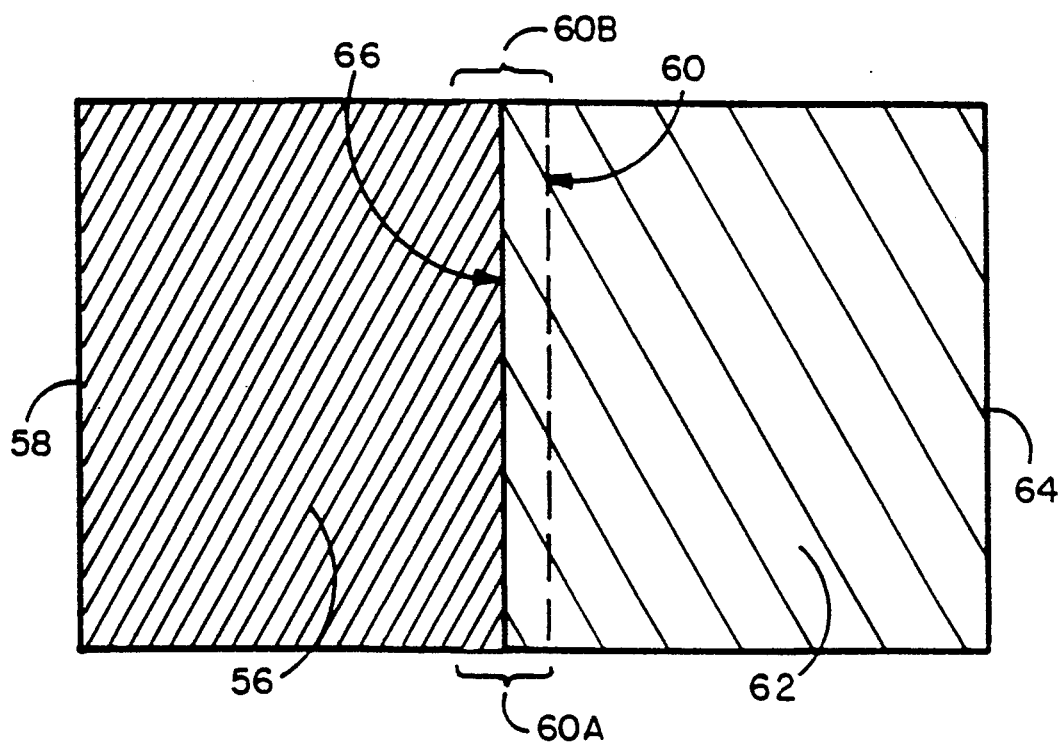
FIG. 7 is a bottom elevated view of the superabsorbent composite of FIG. 6.

A third preferred embodiment of the present invention is illustrated by FIGS. 6-8 respectively. This third embodiment is constructed and formatted for intended use as large, oversized mats and pads often employed as absorbent liners positioned beneath bedsheets, pillowcases, and bedding in general. By the intended positioning and function for these articles, these embodiments are typically rectangular in configuration; often are several feet in dimensions; and are of moderate thickness. Top and bottom elevated views of this third embodiment appear in FIGS. 6 and 7. Cross-sectional views of this third preferred construction illustrating the self-enveloping and self-containing features of the composite as well as the sequence of events for on-demand envelopment and containment of the soiled composite are shown by FIGS. 8A-8D respectively.

Figure 8A:
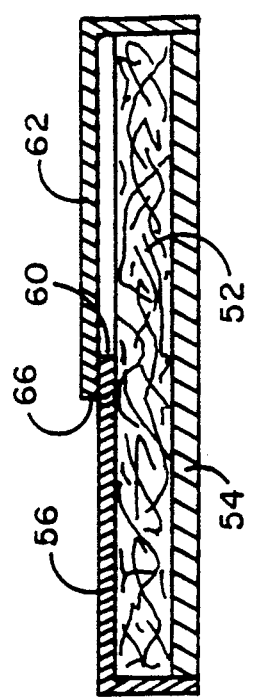
FIGS. 8A-8D are cross-sectional views of the third embodiment of FIGS. 6 and 7 illustrating the sequence of events for converting the superabsorbent composite from the open state into the self-enveloped and self-contained state.

The superabsorbent composite ready for use is shown by FIGS. 5, 7, and 8A. As seen therein, the superabsorbent composite 50 comprises a disposable superabsorbent laminated sheet 51 containing at least one superabsorbent fibrous layer 52 having fluid-absorbing fibers able to absorb not less than 15 times their own weight of fluid; and a fluid-impermeable material 54 applied to one surface of the superabsorbent fibrous layer 52. Disposed beneath the laminated sheet 51 are two planar envelope covers 56 and 62 formed of a fluid-resistant or fluid-impermeable substance. These planar envelope covers 56 and 62 provide the self-enveloping and self-containment capability for the superabsorbent composite 50 as a whole.

As shown in FIGS. 6, 7, and 8A, the envelope cover 56 is configured to be coextensive with the laminated sheet 51 but is dimensioned to cover only slightly more than half the planar surface area of the laminated sheet. Almost three full sides of the perimeter 58 of the envelope cover 56 are joined to the laminated sheet 51 as shown in FIG. 7. Only one full side edge 60 and the adjacent perimeter lengths 60a,60b remain unattached and free. Overlapping the cover 56 at the free edge 60 is the second envelope cover 62. This second cover 62 is also configured to be coextensive with the configuration of the laminated sheet 51 and is also dimensioned to cover only slightly more than one-half of the planar surface area of the laminated sheet. Almost three sides of the perimeter 64 of the cover 62 are also joined to the laminated sheet 52 leaving only the fourth edge 66 unattached and free. In the ready-to-use format of FIGS. 7 and 8A, the free edge 66 of the cover 62 overlaps and retains the unattached edge 60 of the cover 56.

Figure 8B:
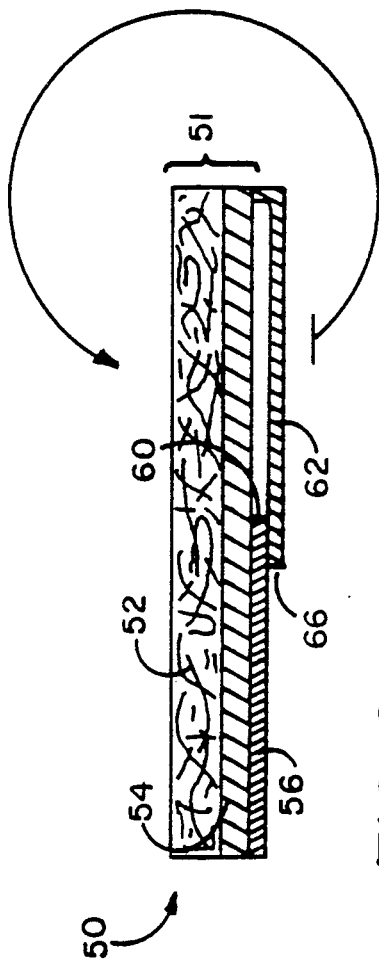
Figure 8C:
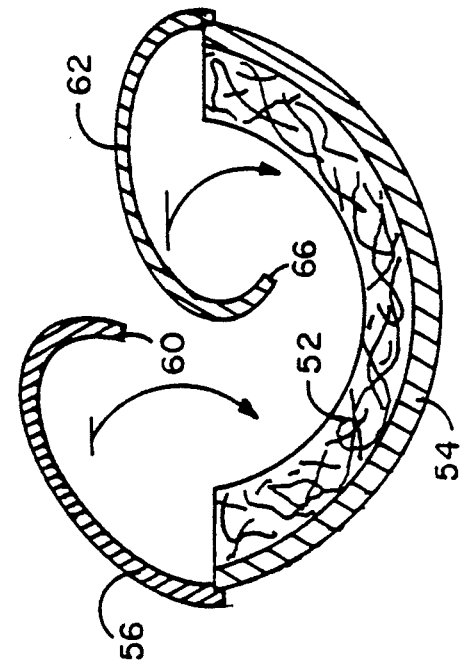
Figure 8D:
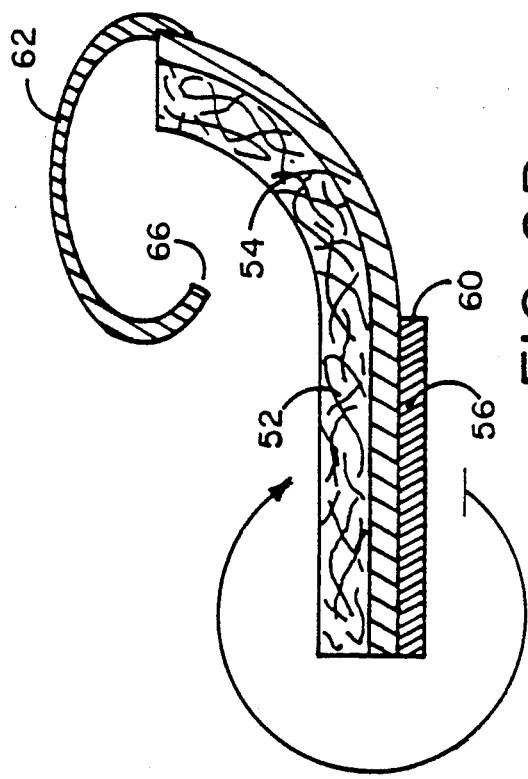

After the superabsorbent composite 50 has served its purpose and is ready to be disposed, the user performs the sequence of events illustrated by FIGS. 8B, 8C, and 8D respectively. Accordingly, the planar envelope cover 62 is topographically reversed and the corresponding portion of the fibrous layer 52 becomes enveloped and contained within the topographically reserved cover 62. Similarly, the planar envelope cover 56 is also topographically reversed and its corresponding portion of the fibrous layer 52 thus also becomes enveloped and contained within the topographically reversed cover 56. After both covers have been topographically reversed, the free edge 60,60a,60b of the cover 56 is again positioned beneath the unattached edge 66 of the cover 62. If desired or required by the user, the free edge 66 as shown in FIG. 8D optionally may then be sealed permanently (using conventionally known means such as sealing tape or adhesive) to the face of the cover 56 thereby forming a fluid-tight, sealed enclosure.

A fourth preferred embodiment is illustrated by FIG. 9 in cross-sectional views. This particular embodiment is constructed and formatted to serve as superabsorbent sheets, blankets, bedding, and the like; and is expected to be dimensioned in large sizes and thicknesses consistent with sheets and blankets commonly employed in hospital beds, stretchers, operating tables, and the like. By the nature of its intended function, these embodiments are expected to be bulky articles which are broad in dimensions and surface area, be relatively thick and dense, and typically weight more than other constructions of the present invention. Moreover, in view of its intended circumstances of use, these embodiments are expected to become heavily soiled—typically with urine, excrement, toxic agents; and under normal conditions be employed to absorb not only infectious blood and lymph fluid, but also sputum and other body fluids normally released by the living person or the corpse subsequently.

The superabsorbent composite constructed and ready for use as sheets, blankets, and other textile-like fabrics appears in cross-sectional view within FIG. 9A. As seen therein, the composite 70 comprises a disposable superabsorbent laminated sheet 72 comprised of at least one superabsorbent fibrous layer 74 comprising fluid-absorbing fibers able to absorb not less than 15 times their own weight of fluid; and a fluid-impermeable material 76 applied to one surface of the fibrous layer 74. The superabsorbent laminated sheet 72 is able to absorb volumes of fluids without leakage through its thickness due to the presence of the fluid-impermeable material 76 applied to the outer surface of the fibrous layer 74. Disposed beneath and attached to a portion of the superabsorbent laminated sheet 72 is a folded or collapsed casing or enclosure 78 formed of flexible, durable, and fluid-impermeable material. As seen in FIG. 9, the folded casing 78 is configured in substantially circular form; nevertheless, the folded casing may be configured and dimensioned in any variety of different forms including polygonal, oval, and/or irregular shapes as the need or circumstances require. It is most desirable that the casing be formed of durable compounds and provide moderate to high tensile strength.

A desirable part of the folded casing 78 is a sealable closure tab 80 which may be opened and closed at will repeatedly as the need or circumstances require. As appearing in FIG. 9A, the folded casing 78 and the sealable closure tab 80 are disposed beneath the laminated sheet 72 only along a portion of its length. However, in alternative embodiments, the folded casing may be of any size or dimensions; accordingly, the casing may be coextensive with the superabsorbent laminated sheet or be dimensioned to be greater in size and surface area than the laminated sheet itself. The degree of the variety is dependent upon and controlled by the user and the intended circumstances of use.

The superabsorbent composite illustrated by FIG. 9A is intended to serve as a substitute for the sheets normally employed as coverings on beds; as a substitute blanket for patients during convalescence; as a replacement for the coverings on operating tables during surgery; and as an alternative to the temporary sheets and blankets used on stretchers, litters, and portable beds employed by ambulances and emergency medical personnel routinely. The laminated sheet 72 will absorb not less than 15 times its own weight in fluid and preferably will absorb more than 50 times its own weight of wastes, liquids, and potentially hazardous contaminants normally encountered. This embodiment is intended to be pre-sterilized before use in many instances; and is also able to be post-sterilized if necessary after use as well.

After the composite 70 has served its purpose and the user has decided to dispose of it, the steps taken prior to disposal are illustrated by FIGS. 9B, 9C, and 9D respectively. As illustrated therein, it is envisioned that the soiled laminated sheet 72 will be of such size, weight, and surface area as to be too cumbersome and heavy to be carried as a flat article; and thus consequently will be folded loosely into a bundle or mass. Such folding or bundling can cause the retained fluids and other liquid wastes previously absorbed by the laminated sheet to become partially enclosed within the laminated sheet itself, thereby adding an extra measure of control to the attending personnel; and also permits the folded bundle to be more easily moved or carried for ultimate disposal.

Accordingly, as shown within FIG. 9B, the soiled laminated sheet 72 is purposefully folded upon itself to form a compact bundle; and the casing 78 is unfolded to its fullest volume and the closure tab 80 detached in order to access the interior volume of the casing 78. Once unsealed and opened, the casing 78 is then wrapped around the folded laminated sheet 72 by the user as illustrated by FIG. 9C. By continuing the envelopment of the folded laminated sheet 72 to completion, the unfolded casing completely envelopes and contains the bundled laminated sheet 72 entirely. Moreover, by reattaching the closure tab 80 after enveloping the entirety of the laminated bundle, the casing 78 not only envelopes and contains the soiled laminated sheet but also completely and effectively seals and separates the soiled sheet from the ambient environment as illustrated by FIG. 9D. In this fourth preferred embodiment, the casing 78 and the sealable closure tab 80 provide the enveloping and containing means on-demand by which the laminated sheet may be encompassed and enclosed effectively and completely. The soiled laminated sheet 72, now completely enveloped and contained within the casing 78, may now be sterilized if desired prior to disposal; or may be disposed without post-sterilization in accordance with routine practice.

In order to provide a more complete understanding of the present invention as a whole, each of the component parts of the superabsorbent composite will now be further described in detail.

The Superabsorbent Laminated Sheet

Details regarding the preferred laminated sheet embodiment of the fibrous layer are illustrated by FIGS. 10-13 respectively. FIG. 10 shows a perspective view of the superabsorbent fibrous sheet 100 as a multi-laminate construction. As illustrated, the fibrous sheet 100 is most desirably formed as a three part laminate comprising a fluid-permeable, covering stratum 102 having representative pores 103 to indicate the fluid permeable nature of the covering. Underlying this fluid permeable covering stratum 102 is the superabsorbent fibrous layer 104 comprising fluid-absorbing fibers able to absorb at least 15 times their own weight of fluid. The preferred form and embodiment of these superabsorbent fibers is as a non-woven absorbent batt composed of a substantially uniform array of superabsorbent fibers 106 (able to absorb not less than 15 times their own weight of fluid) and support fibers 108. While the primary function of the superabsorbent fibers 106 is to absorb high volumes of fluid, the support fibers 108 interlock with the superabsorbent fibers to provide strength and stability for the superabsorbent fibrous batt both before and after it is saturated by fluid. The support fibers 108 also provide good absorbent and adsorbent qualities and offer good resiliency when either in wet or dry states. In general, the superabsorbent fibers 108 typically comprise between 5-50% of the total fiber content for the non-woven absorbent batt. Lastly, a fluid-impermeable, supporting material 110 is preferably bonded in a conventionally known manner to the underside of the absorbent batt 104. This fluid-impermeable, supporting material 110 acts to prevent passage and/or transport of fluid previously absorbed in the absorbent batt from passing onto any other surface or material.

The multi-laminate sheet construction preferred for use as the superabsorbent fibrous format may be manufactured and supplied in roll form as shown by FIG. 11. In this construction and manufacture, the fluid-impermeable supporting material 110 (serving primarily as an impermeable bottom layer for the multi-part construction) may be extended along the sides and edges of the non-woven absorbent batt and be extended to overlay the top edges of the fluid-permeable covering stratum 102—thereby providing peripheral side shields 112 and 114 for the multi-laminate construction as a whole. In keeping with the optional replaceable and disposable formats for the superabsorbent fibrous layer 104 as described previously, FIG. 11 illustrates a roll of the preferred three part constructed, superabsorbent laminated sheet—a specific dimensioned segment of which is removed by cutting along the line aa' as indicated. Subsequently, the freshly cut ends of the three-part laminated sheet may then also be optionally folded over along its edges as illustrated to provide additional side shields 116 and 118. Accordingly, as seen in FIG. 12, the protective side shields 112, 114, 116, and 118 respectively would provide additional but optional effective barriers against the overflow of fluids or liquids absorbed by the absorbent batt 104 and maintain the overall integrity, strength, and multi-laminate construction of the superabsorbent sheet 100.

It will be noted and appreciated that the preferred multi-laminate construction for the superabsorbent three-part laminated sheet as described herein is part of the subject matter described and claimed within copending patent application of Conrad A. D'Elia and John D. Hogan entitled "Superabsorbent Non-woven Fibrous Material," the text of which is expressly incorporated by reference herein. In addition, the most preferred composition and blend of fiber materials to be described subsequently also comprises a major part of the above identified, copending patent application. Preferably, the superabsorbent fibers employed in the non-woven absorbent batt within the multi-laminate construction is a fiber formed from a blend of heterocyclic carbonate and a copolymer of maleic anhydride and isobutylene, as described in U.S. Pat. Nos. 4,616,063; 4,705,773; 4,731,067; 4,743,244; 4,788,237; and 4,813,945 respectively—the text of which are also individually incorporated by reference herein for their disclosures.

For optimal absorptive function by the non-woven absorbent batt, the superabsorbent fibers are mixed with support fibers, preferably using several deniers of polyester. A variety of other materials and compositions may also be used for the support fibers themselves. These include: rayon, cotton, polypropylene, nylon, and polyethylene. These support fibers, regardless of specific composition or materials, should interlock with the superabsorbent fibers, preferably in a non-woven manner. In addition, although a great range of percentage content for the support fibers may be utilized, the percentage ratio of support fibers typically comprises 50-95% of the total fiber content for the absorbent batt.

The fluid absorption characteristics and volume capacity of the superabsorbent fibrous layer and the three-part laminated sheet (as noted by the disclosure within copending application of Messers. D'Elia and Hogan) are determined by many factors including superabsorbent fiber content, the composition of the support fiber material, batt density and padding size. It is recognized also that the horizontal and vertical water retention properties of the absorbent fibrous layer will vary markedly with alterations in the nature and percentage content of superabsorbent fiber versus support fiber, the denier, the fabric weight, and the composition of the support fiber. If and when the preferred blend of heterocyclic carbonate and copolymer of maleic anhydride and isobutylene is employed, polyester is the most desirable material for use as the support fiber for combination with the superabsorbent fiber. Polyester contributes excellent absorbency properties adjunct and complementary to those of the absorption fibers themselves when present in sufficient density. Moreover, whenever finer denier of support polyester fibers is employed, the overall fluid retention capacity is clearly increased such that various embodiments of the preferred materials are able to absorb 60 fold and sometimes up to 100 fold their product weight of water or other fluid.

To illustrate and to understand how the multi-laminate preferred construction for the superabsorbent fibrous layer works, FIG. 13 illustrates a cross-sectional view of the multi-laminate construct in greater detail.

The support fibers 108 are shown as solid lines while the superabsorbent fibers 106 are provided as dashed lines so that they can be distinguished from one another. The fluid-permeable covering stratum 104 permits the migration of fluids such as water and is typically hydrophobic to facilitate complete and rapid migration and transfer of fluid to the absorbent batt beneath it. An added and desirable function of the covering stratum 102 is to provide a smooth sliding surface of low surface tension which presents a relatively small coefficient of friction upon which the skin of the patient, organs, or instruments may be readily moved without tearing the absorbent batt material whether in dry or saturated form. The fluid impermeable supporting material 110 acts as a bottom sheet and is desirably any suitably water-impervious and tear resistant material. This fluid-impermeable material 110 may be folded, corrugated, or embossed to facilitate an increased wicking of fluid through the absorbent batt thereby encouraging effective distribution of absorbed fluid throughout the entirety of the absorbent batt. In the unused, dry state, both the superabsorption fibers and the support fibers may criss-cross and bend as indicated within FIG. 13. When the absorbent batt absorbs fluid and becomes wet, the superabsorbent fibers 100 can swell to many times their original dry size, up to and including about 100 times their diameter when dry. In addition, the swelling of the superabsorbent fibers upon wetting exerts force upon the support fibers 108 in the batt and stiffens them. Accordingly, in many instances, the absorbent batt forces fibers which are only loosely crossed and meshed in the dry state to tightly lock and support each other in the wetted fluid absorbent state. This mechanism is believed to account in part at least for the superabsorption capability of the fibrous layer to retain its physical integrity even when holding many times its weight in fluid.

It should be noted and appreciated also that a wide range and diversity of other compounds and chemical compositions are believed to be conventionally available as substitutes and replacements for the preferred composition for superabsorbent fibers as described above. The range, variety, and diversity of such superabsorbent materials and compositions is described within the following publications: water absorbing acrylic copolymer compositions prepared from acrylic acid monomers and hydrophilic unsaturated carbonate monomers as described within Japanese Patent Publication No. 63242344(881017); the water absorptive composites of impregnated natural or synthetic fibers with modified acrylic acid described within European Patent Publication No. 290814(881117); water-swellable cross-linked polymers of vinyl-saccharide monomer as described by European Patent Publication No. 283090(880921); a super-absorbent for blood and proteinaceous fluid comprising insoluble ionic macromolecular material in acidic form as described within French Patent No. 2602985(880226); water absorptive fibrous composite materials containing polymerized partially neutralized acrylic acid which is cross-linked using glycidyl ether compounds as described by European Patent Publication No. 262405(880406); an absorbent fibrous material comprising cross-linked polysaccharides as described in European Patent Publication No. 232121(870812); water-absorbing polymer compounds prepared by polymerization of acrylic acid (alkali metal) salts in the presence of alpha-olefins and carboxylic acids as described within Japanese Patent Publication No. 62053310(870309); and a fluid absorbing composition comprising water soluble carboxylic polyelectrolyte cross-linked with di- or poly-functional aziridine as described within U.S. Pat. No. 4,645,789.

It will be recognized and appreciated that the provided listing is merely illustrative and clearly non-exhaustive in its coverage. Many other fluid absorbing materials able to be manufactured and to provide a superabsorbent capability—that is, able to absorb at least 15 times its own weight in fluid—are clearly available and commercially sold today. All such conventionally known chemical compositions, manufacturers, and superabsorbent materials are deemed to be within the scope of the present invention.

On-Demand Enveloping And Containing Means

Via the preferred embodiments illustrated by FIGS. 1–9 respectively, it will be recognized that the enveloping and containing means, at a minimum, will take form as a fluid-impermeable supporting cover or stratum which is purposefully designed and constructed to be able to envelope and contain the superabsorbent fibrous layer or the preferred superabsorbent laminated sheet construction on-demand. Desirably, the supporting cover or stratum will be composed of flexible materials; be durable in such degree that the length of service for the gauze commodity is not hampered or diminished by the construction or materials forming the supporting cover; and be sufficient in tensile strength that it can support the weight of the superabsorbent fibrous layer or superabsorbent laminated sheet construction over extended uses even while the retained fluids are at a maximum volume or quantity. In addition, it is most desirable that the materials forming the supporting cover or stratum be relatively light weight, be moisture resistant, and be easily malleable. The most preferred compositions for use are thus olefins and polymeric compositions such as nylon, polyethylene, polypropylene, polyacrylics, polyamides, and other heat resistant compounds, polymers, and materials. Moreover, it is desirable that these materials be hydrophobic rather than hydrophilic; and that they be sufficiently durable to withstand at least one form of conventionally known sterilization procedures including heat sterilization, gaseous sterilization, and gamma radiation sterilization.

As will be recognized and appreciated via the various embodiments previously described herein, the actual mode of construction and the format employed for the supporting cover or stratum material is a matter of subjective design, individual discretion, and personal choice of the manufacturer or user. The supporting cover or stratum may be formed as a single sheet or multiple sheet construction if this is considered useful; and may be folded or collapsed and subsequently erected into full volume or size once or repeatedly as needed. Equally important, the manner or mode of juncture for the supporting cover to the superabsorbent fibrous layer or the superabsorbent laminated sheet is merely a matter of personal design and/or construction preferences. It is required only that the enveloping and containing means be joined to at least a portion of the superabsorbent fibrous layer or the superabsorbent laminated sheet. The degree of juncture (partial or complete), the mode of attachment (temporary or permanent), the ode and procedure of envelopment and containment, and the kind and sequence of manipulative steps by which the enveloped and contained article becomes enclosed is merely a matter of personal choice and convenience to the user. A meaningful degree of variety in this has been effectively disclosed and demonstrated by the preferred embodiments illustrated within FIGS. 1–9 respectively. For these reasons, it is deemed that regardless of how simplistic or complicated the actual construction, design, configuration, dimensions, or materials employed for any embodiment, so long as discrete and identifiable enveloping and containing means are joined to at least a portion of the superabsorbent fibrous layer or the superabsorbent laminated sheet, the essential requirement of the present invention is met and satisfied.

On-Demand Closure Means

The third essential component and requirement of the superabsorbent composite which is the present invention is the presence of on-demand closure means joined to the enveloping and containing means for closure of the superabsorbent fibrous layer or superabsorbent laminated sheet after envelopment and containment. The present invention presumes and intends that all the conventionally known articles, compositions, constructions, and fabrications which are commonly employed for closure purposes generally are available for use within the present invention. Accordingly, the on-demand closure means may optionally include sealing components and features which allow and cause the enveloped and contained superabsorbent fibers to become sealed fluid-tight as part of the closure. For this purpose, adhesive compositions regardless of formulation, manner of application, and permanency of adherence are expected to be a favored means of closure. In addition, closure means which may be closed and opened repeatedly without failure or loss such as overlapping raised ribs and enveloping cavities commonly seen in "zip lock" closures as well as other interlocking components made of plastics or other resilient materials are intended to be employed for this purpose routinely. In certain instances also, zipper-like constructions, folded-over seams and edges, and self-binding leads and extensions are all expected to be applicable and useful as parts of the composite construction. All of these known closure devices and systems are deemed to be within the scope of the present invention regardless of their individual design, construction, materials, or requisites for attachment to the enveloping and containing means as such.

The present invention is not to be limited in scope nor restricted in form except by the claims appended hereto.

What I claim is:

1. A disposable, superabsorbent composite which is self-enveloping and self-containing on-demand, said composite comprising:
    at least one disposable superabsorbent fibrous layer comprising fluid-absorbing fibers able to absorb not less than 15 times their own weight of fluid wherein said superabsorbent fibrous layer does not substantially release said fluid after absorption;
    disposable, on-demand enveloping and containing means joined to at lest a portion of said superabsorbent fibrous layer, said means being able to envelop and contain said superabsorbent fibrous layer on-demand; and
    disposable, on-demand closure means joined to said enveloping and containing means for closure of said enveloped and contained superabsorbent fibrous layer on-demand.

2. A disposable, superabsorbent composite which is self-enveloping and self-containing on-demand, said composite comprising:
    a disposable superabsorbent laminated sheet comprised of:
      (a) at lest one superabsorbent fibrous layer comprising fluid-absorbing fibers able to absorb not less than 15 times their own weight of fluid wherein said superabsorbent fibrous layer does not substantially release said fluid after absorption, and
      (b) a fluid-impermeable material applied to one surface of said superabsorbent fibrous layer;
    disposable, on-demand enveloping and containing means joined to at least a portion of said superabsorbent laminated sheet, said means being able to envelop and contain said superabsorbent laminated sheet on-demand; and
    disposable, on-demand closure means joined to said enveloping and containing means for closure of said enveloped and contained superabsorbent laminated sheet on-demand.

3. The composite as recited in claim 1 or 2 further comprising a fluid-permeable covering stratum applied to one surface of said fibrous layer.

4. The composite as recited in claim 1 or 2 wherein said superabsorbent fibrous layer comprises a mixture of support fibers and said fluid-absorbing fibers.

5. The composite as recited in claim 4 wherein said mixture of fibers comprises a non-woven array of fibers.

6. The composite as recited in claim 4 wherein said support fibers comprise a polyester compound.

7. The composite as recited in claim 1 or 2 wherein said fluid absorbing fibers comprise a heterocyclic carbonate and a copolymer of maleic anhydride and isobutylene.

8. The composite as recited in claim 1 or 2 wherein said superabsorbent fibrous layer can absorb up to 50 times its own weight of fluid.

9. The composite as recited in claim 1 or 2 wherein said superabsorbent fibrous layer has been sterilized in advance of use.

10. The composite as recited in claim 1 or 2 wherein said enveloped and contained superabsorbent fibrous layer is sterilized prior to disposal.

11. The composite as recited in claim 1 wherein said superabsorbent laminated sheet further comprises a durable planar layer of material positioned adjacent to said fluid-impermeable supporting material.

* * * * *